United States Patent
Brown et al.

(10) Patent No.: US 11,815,477 B2
(45) Date of Patent: Nov. 14, 2023

(54) NON-DESTRUCTIVE DETECTION OF SURFACE AND NEAR SURFACE ABNORMALITIES IN A METALLIC PRODUCT

(71) Applicant: THE UNIVERSITY OF SHEFFIELD, Sheffield (GB)

(72) Inventors: Matthew Brown, Sheffield (GB); Peter Lawrence Crawforth, Sheffield (GB); Bradley Peter Wynne, Glasgow (GB); Hassan Ghadbeigi, Sheffield (GB)

(73) Assignee: THE UNIVERSITY OF SHEFFIELD, Sheffield (GB)

( * ) Notice: Subject to any disclaimer, the term of this patent is extended or adjusted under 35 U.S.C. 154(b) by 108 days.

(21) Appl. No.: 17/606,995

(22) PCT Filed: Mar. 25, 2020

(86) PCT No.: PCT/GB2020/050795
§ 371 (c)(1),
(2) Date: Oct. 27, 2021

(87) PCT Pub. No.: WO2020/221986
PCT Pub. Date: Nov. 5, 2020

(65) Prior Publication Data
US 2022/0205934 A1 Jun. 30, 2022

(30) Foreign Application Priority Data
Apr. 30, 2019 (GB) .................................. 1906037

(51) Int. Cl.
*G01N 23/207* (2018.01)
*G01N 23/20* (2018.01)
(Continued)

(52) U.S. Cl.
CPC ....... *G01N 23/2073* (2013.01); *G01N 23/207* (2013.01); *G01N 23/20025* (2013.01);
(Continued)

(58) Field of Classification Search
CPC ..... G01N 2223/1003; G01N 2223/204; G01N 2223/646; G01N 2223/6462;
(Continued)

(56) References Cited

U.S. PATENT DOCUMENTS

| 5,835,220 A | 11/1998 | Kazama et al. |
| 2009/0290681 A1 | 11/2009 | Je et al. |

(Continued)

FOREIGN PATENT DOCUMENTS

| EP | 1 494 275 A1 | 1/2005 |
| EP | 2 903 397 A1 | 8/2015 |

(Continued)

OTHER PUBLICATIONS

PCT International Search Report for PCT/GB2020/050795, dated Jul. 16, 2020, 4 pages.

(Continued)

*Primary Examiner* — Mark R Gaworecki
(74) *Attorney, Agent, or Firm* — Merchant & Gould P.C.

(57) ABSTRACT

A method of non-destructive detection of surface and near surface abnormalities in a metallic product. The method comprises positioning a sample having a surface under a source of an incident radiation. The surface of the sample is then irradiated with the incident radiation from the source. A scattered radiation is detected and a radiation pattern from the detected scattered radiation is produced. Said radiation pattern is then analysed and the output indicative of the scattered radiation from the sample is produced. Said produced output is then compared with a threshold value, the threshold value indicative of a maximum acceptable (Continued)

Figure 1:
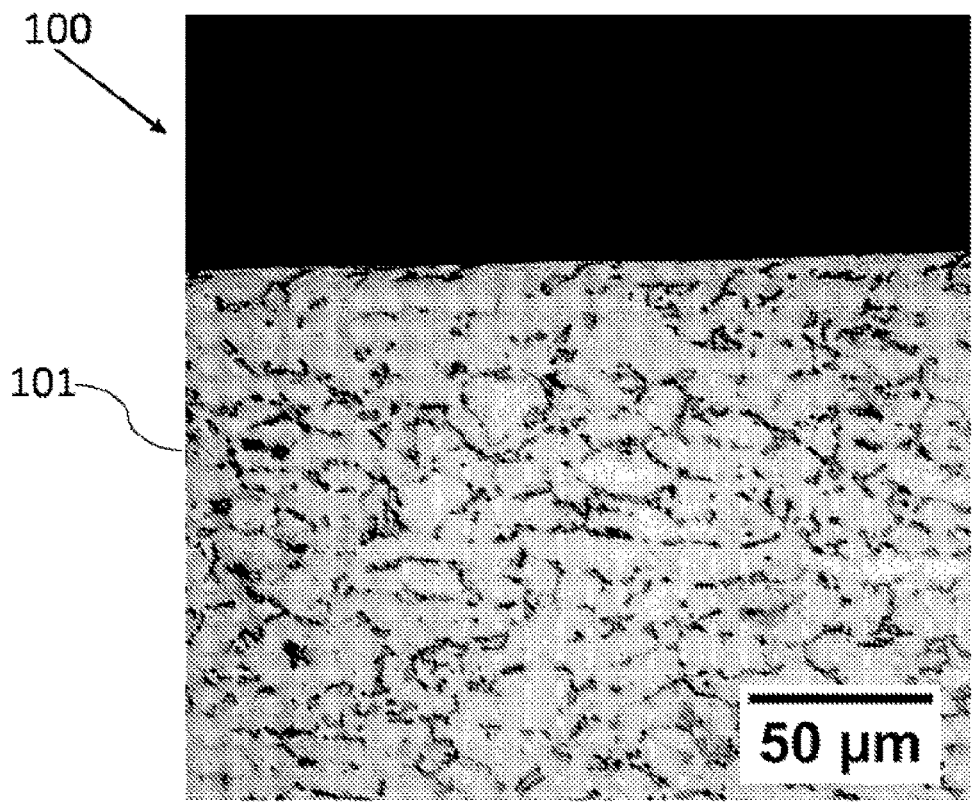

detected surface abnormality. Finally, the presence of a surface abnormality is identified when the output exceeds the threshold value.

16 Claims, 8 Drawing Sheets

(51) Int. Cl.
  *G01N 33/20* (2019.01)
  *G01N 23/20025* (2018.01)
  *G01N 33/2045* (2019.01)
(52) U.S. Cl.
  CPC ......... *G01N 33/20* (2013.01); *G01N 33/2045* (2019.01); *G01N 2223/1003* (2013.01); *G01N 2223/204* (2013.01); *G01N 2223/646* (2013.01); *G01N 2223/6462* (2013.01)
(58) Field of Classification Search
  CPC ........... G01N 23/20025; G01N 23/207; G01N 23/2073; G01N 33/20; G01N 33/2045
  See application file for complete search history.

(56) References Cited

U.S. PATENT DOCUMENTS

| 2010/0332153 | A1 | 12/2010 | Vegter et al. |
| 2019/0003987 | A1* | 1/2019 | Fukui ................. G01N 21/8914 |

FOREIGN PATENT DOCUMENTS

| EP | 3 147 653 A1 | 3/2017 |
| EP | 3 364 173 A1 | 8/2018 |
| JP | H11295241 A | 10/1999 |

OTHER PUBLICATIONS

PCT Written Opinion of the ISA for PCT/GB2020/050795, dated Jul. 16, 2020, 6 pages.
Combined Search and Examination Report for GB10906037.5, dated Oct. 24, 2019, 7 pages.
Yoshiharu Ueyama et al: "Recent Technology of Preventive Maintenance for Pumps", Hitachi Review, Hitachi Ltd. Tokyo, JP, vol. 40, No. 2, Apr. 1, 1991 (Apr. 1, 1991), pp. 127-134, XP000264679, ISSN: 0018-277X.

* cited by examiner

NON-DESTRUCTIVE DETECTION OF SURFACE AND NEAR SURFACE ABNORMALITIES IN A METALLIC PRODUCT

RELATED APPLICATIONS

This application is a National Phase entry of PCT Application No. PCT/GB2020/050795 filed Mar. 25, 2020, which application claims the benefit of priority to GB Application No. 1906037.5, filed Apr. 30, 2019, the entire disclosures of which are incorporated herein by reference.

TECHNICAL FIELD

This invention relates to a method of non-destructive detection of surface and near surface abnormalities in a metallic product.

BACKGROUND

There is a need to provide a method of detecting machining-induced abnormalities non-destructively, particularly in the fields of aerospace or railway engineering, for example.

White layer, otherwise known as amorphous layer, nanocrystalline layer, white etching layer, adiabatic shear band, severely plastically deformed layer, or heat affected layer, is a surface or near surface abnormality that may be formed in the metal or metal alloy during the machining process. Machining processes include, amongst others, milling, drilling, grinding, broaching, or electrical discharge machining. White layer can have a detrimental effect on the machined parts' performance due to altered mechanical and microstructural properties of the resultant machined part, in particular reduced fatigue life. White layers are usually found in the region of the surface of the post-machined parts, white layers typically have a thickness lying in the range of microns to the tens of microns. White layer regions receive their name due to their appearance when viewed through an optical microscope. It is generally assumed that the white or slightly off-white colour is due to light-scattering off the constituent grains in the layer.

It is commonly believed that the white layer formed during the machining process is caused by either phase transformation, by grain refinement through severe plastic deformation or by surface chemical reactions. In some cases, the formation of white layer may be enhanced by either high cutting speeds or when cutting using worn tools.

Current detection methods typically involve preparing a specimen from the machined samples by inspecting prototype parts before the production line or taking a part, from a batch of parts, off the production line, preparing the part for analysis (sectioning, grinding and polishing) and further analysing the part in the lab using microscopy.

Figure 2:
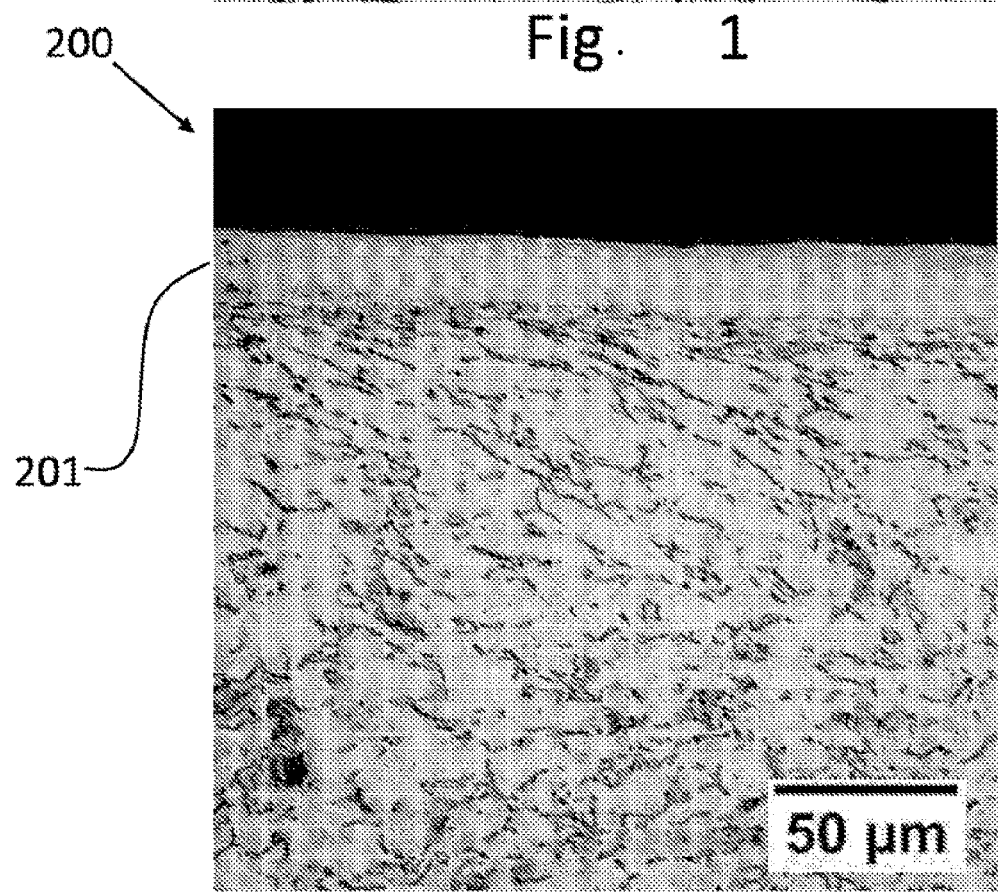

One such technique is cross-sectional microscopy. This process assesses the cross-section of a part. FIG. 1 is the representative example of a specimen (100) sample of a part (i.e. a section of part) with no surface abnormalities (101) present. FIG. 2 is a specimen (200) having white layer (201) formed on the machined surface due to the deformation of material caused by rubbing of the cutting tool on the workpiece.

Despite being suitable for assessment of white layer, the optical microscopy method of analysis is costly and unsuitable for an automated inspection as the method:

i) involves interruption of the production streamline;
 ii) requires destruction of the part of the machined surface from the batch;
 iii) cannot be employed for streamlined manufacturing as being notably time-consuming as well as incurring additional expenses;
 iv) cannot test all parts as the method is a destructive technique, therefore there is a risk that untested parts will have abnormalities present.

It is desirable to provide an alternative non-destructive characterisation method for assessing the white layer and other surface or near surface abnormality formation during machining processes.

It is an object of embodiments of the invention to at least mitigate one or more of the problems associated with the prior art.

STATEMENTS OF INVENTION

Aspects and embodiments of the invention provide a method of non-destructive detection of surface and near surface abnormalities in a metallic product, as claimed in the appended claims.

According to an aspect of the invention, there is provided a method of non-destructive detection of surface and near surface abnormalities in a metallic product, the method comprising:

positioning a sample having a surface under a source of an incident radiation;
 irradiating the surface with the incident radiation from the source;
 detecting a scattered radiation;
 producing a radiation pattern from the detected scattered radiation;
 analysing the radiation pattern;
 producing an output indicative of the scattered radiation from the sample;
 comparing the output with a threshold value, the threshold value indicative of a maximum acceptable detected surface abnormality; and
 identifying the presence of a surface abnormality when the output exceeds the threshold value.

Advantageously, the method allows assessment of the presence of unwanted abnormalities on the surface of the metallic machined objects, by comparing the produced output with a pre-established threshold value, below which no or an acceptable/tolerable level of abnormality is present in the sample.

In an embodiment, a threshold value is derived from one or more reference samples with no surface abnormality present. Advantageously, this provides a reference value that can be further used when analysing a sample with an unknown structure.

In an embodiment, said surface abnormality is induced by machining, friction, shaping or forming.

In yet another embodiment, said surface abnormality is one or more of a white layer, white etching layer, amorphous layer, and/or thermo-mechanically deformed region.

In an embodiment, said incident radiation includes at least one of X-ray radiation, laser radiation, and/or neutron radiation. Advantageously, by employing various radiation sources it is possible to obtain the results from different radiation/matter interactions and, in turn, to analyse the products with various compositions over different volumes/depths of material in the near-surface.

In an embodiment, the output is an intensity value corresponding to an intensity of the detected scattered radiation.

In yet another embodiment, the output is derived from the intensity ratio of one or more scattered radiation peaks. This is advantageous as it allows detection of samples with a white layer by showing that the surface has a different texture, i.e. one crystallographic orientation is favoured over another. Using more than one peak allows selection of the peaks which give the greatest distinction to the baseline sample.

In yet another embodiment, the threshold value is derived from the intensity of one or more scattered radiation peaks of the one or more reference samples with no surface abnormality present. In order to determine whether the abnormality is present, there has to be a reference value that is used as a threshold for assessing the presence/absence of the white layer. A number of reference samples can be obtained and analysed to be subsequently collectively used as a threshold value, the threshold value being indicative of "good" samples with no or tolerable amount of surface or near surface abnormality present.

In an embodiment, the threshold value is derived from the intensity ratio of one or more scattered radiation peaks. Once the reference samples have been obtained and analysed, the intensity of the scattered radiation peaks is detected. Advantageously, this intensity can be used as a term of comparison with the intensity of the scattered peaks of the machined samples with unknown surface structure. By comparing with a sample without defect it is possible to set this threshold level which can then be used as an indicator for the presence of white layer if it is exceeded in an unknown surface.

Alternatively, the output is derived from a width of a scattered radiation peak corresponding to the scattered radiation. Estimating the width of the produced radiation peaks allows the resulting values to be used as a comparison means with the widths of the peaks of the samples with unknown structure.

In the further alternative, the threshold value is derived from one or more widths of the one or more scattered radiation peaks of the one or more reference samples with no surface abnormality present. Advantageously, this allows for more precise measurements. That is, when a plurality of samples with no or a tolerable level of surface abnormality present are used as reference samples, the measurement accuracy is improved.

In an embodiment, the output is obtained by using filtered monochromatic X-rays. Advantageously, this allows the production of diffraction peaks by constructive interference of a monochromatic beam of projected X-rays scattered from the lattice planes of the samples.

In an embodiment, the output is obtained by scanning with a detector through a range of angles. Preferably, scanning across the range of angles allows detection of multiple peaks originating from the same sample, and to use alternative peak intensities when some of the most commonly used intensities are hindered or not present in the resultant radiation pattern from the sample. In an embodiment, the range of angles is 2θ.

In an embodiment, the output is obtained by arranging the detector at a fixed angle. Advantageously, this allows the analysis time to be shortened by scanning at an angle where the intensity of the output from the sample is predicted/known to be at its highest, thus avoiding the need to scan through the full range of angles. This limitation of the scanning angle, that is generally slightly above the total reflection angle of the material, further allows analysis of thin film samples.

In an embodiment, the source of monochromatic X-ray is any one of copper, iron, molybdenum, chromium, manganese, silver or cobalt. A number of X-ray sources can be advantageously employed for diffraction studies, thus covering the possibilities to study samples with a variety of properties and structures.

In an embodiment, the output is obtained using polychromatic X-rays. Using polychromatic X-rays advantageously allows X-ray diffraction techniques to be employed with a polychromatic beam in energy-dispersive mode (EDX) as it negates the need for a goniometer to scan over a range of angles. Moreover, energy-dispersive XRD is less sensitive to a sample shape which allows analysis of the samples of various shapes and sizes.

In an embodiment, said sample comprises any alloy from the list: titanium, nickel, iron, aluminium.

Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. The applicant reserves the right to change any originally filed claim or file any new claim accordingly, including the right to amend an originally filed claim to depend from and/or incorporate any feature of any other claim although not originally claimed in that manner.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

LIST OF FIGURES

Figure 3:
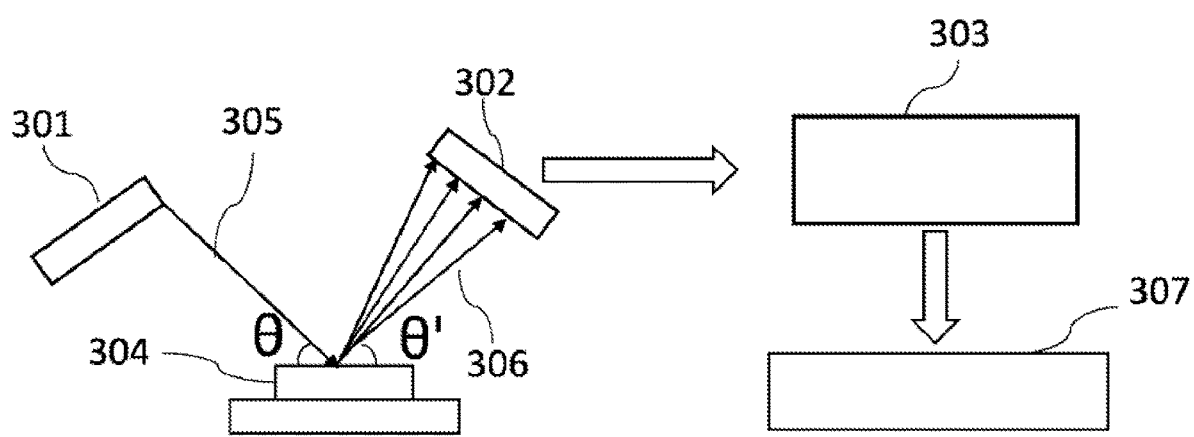
Figure 4:
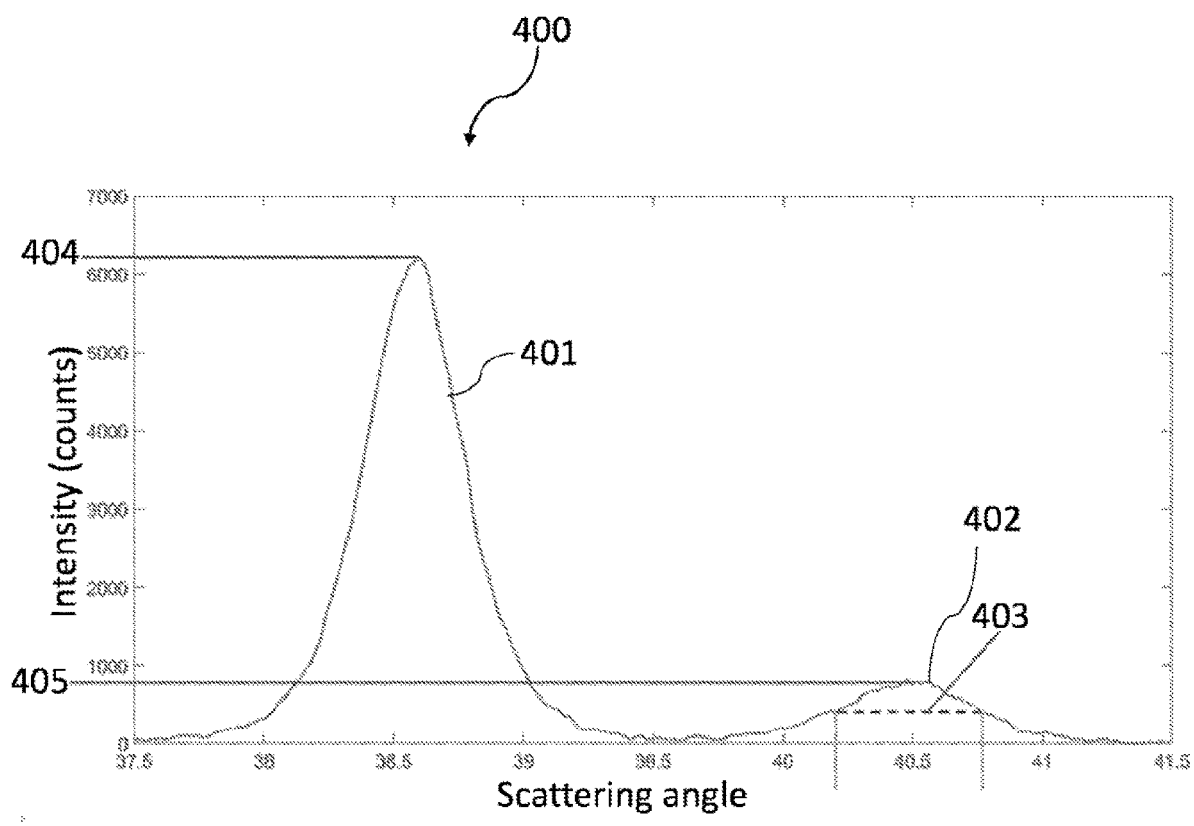
Figure 5:
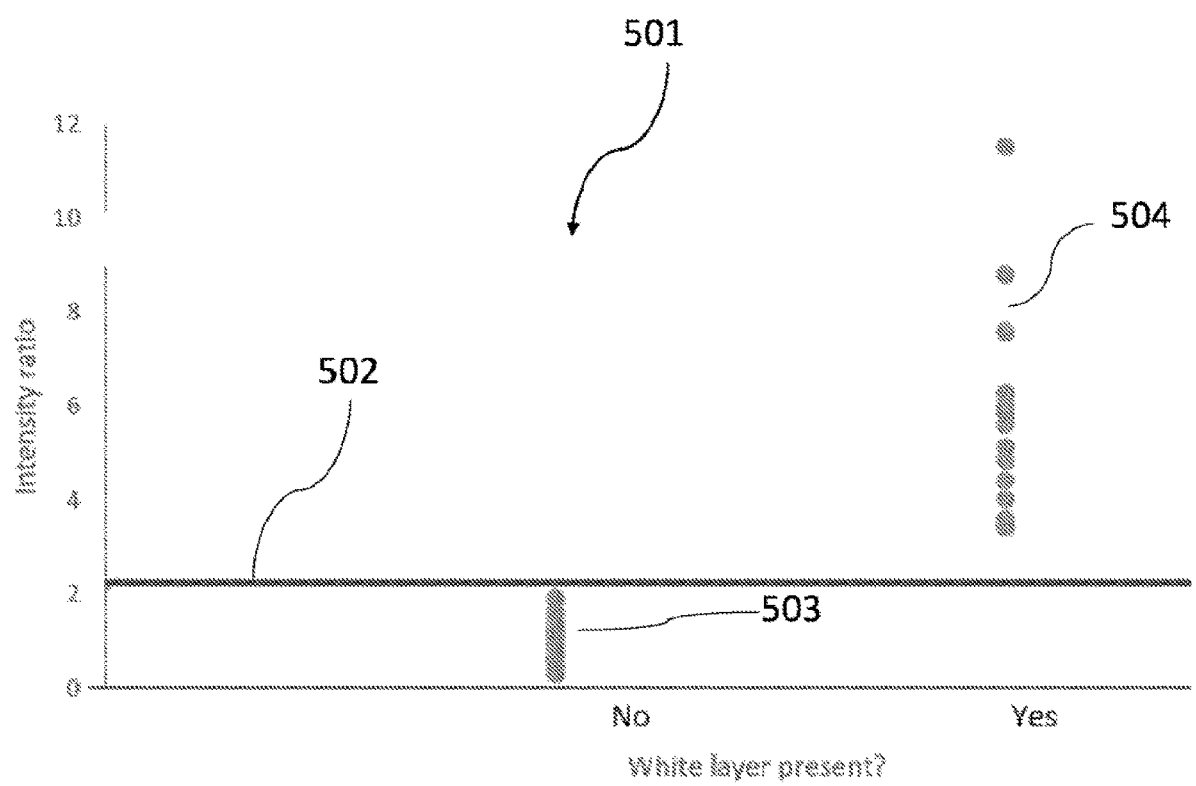
Figure 6:
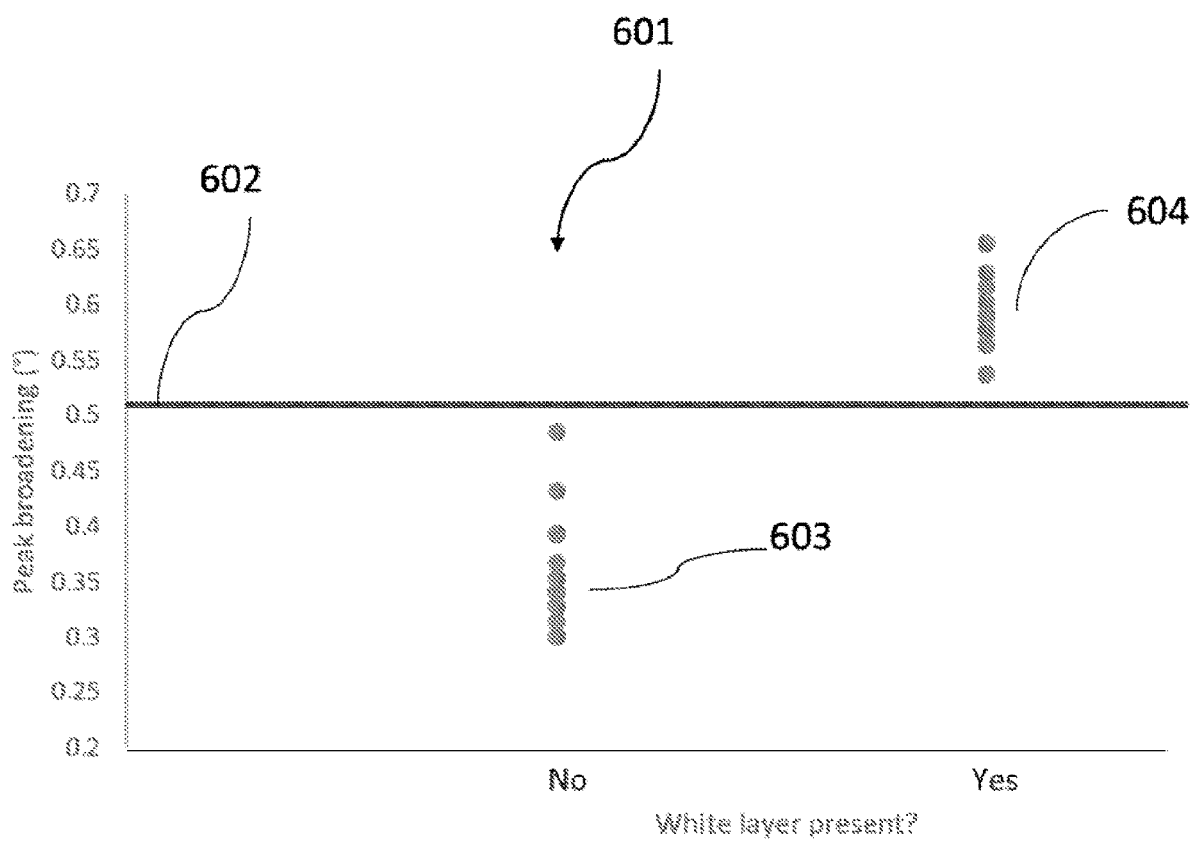
Figure 7:
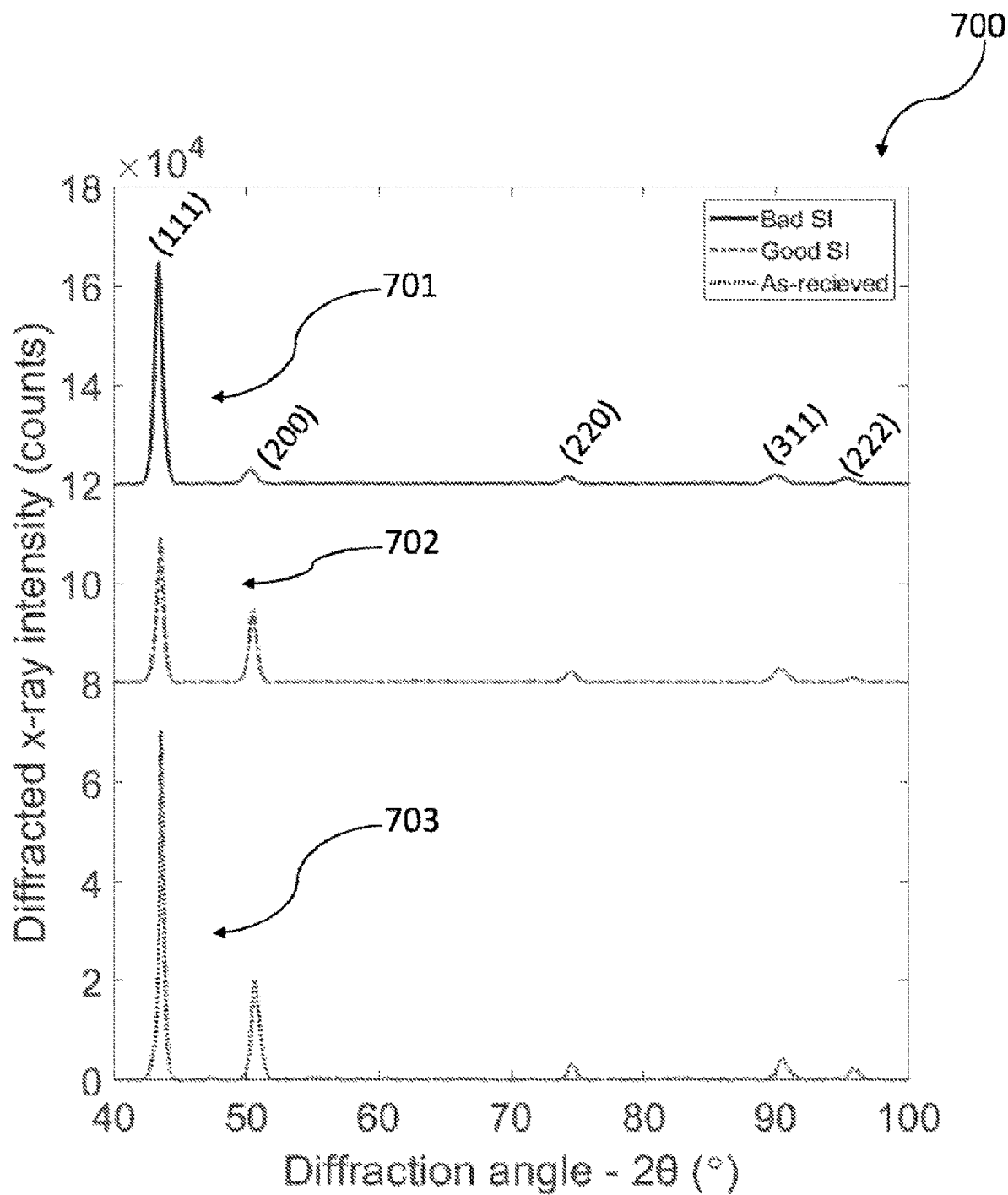
Figure 8:
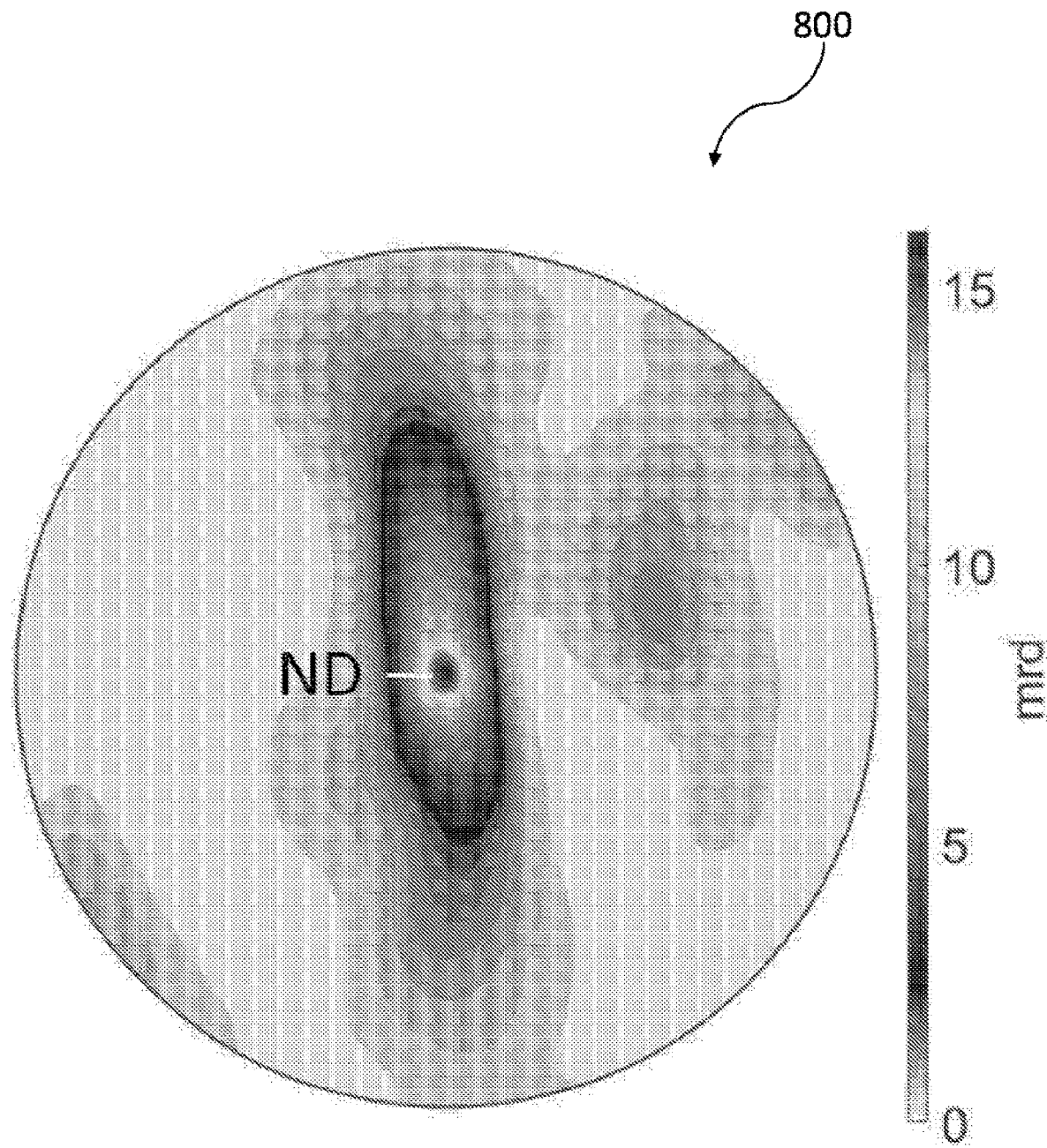
Figure 9:
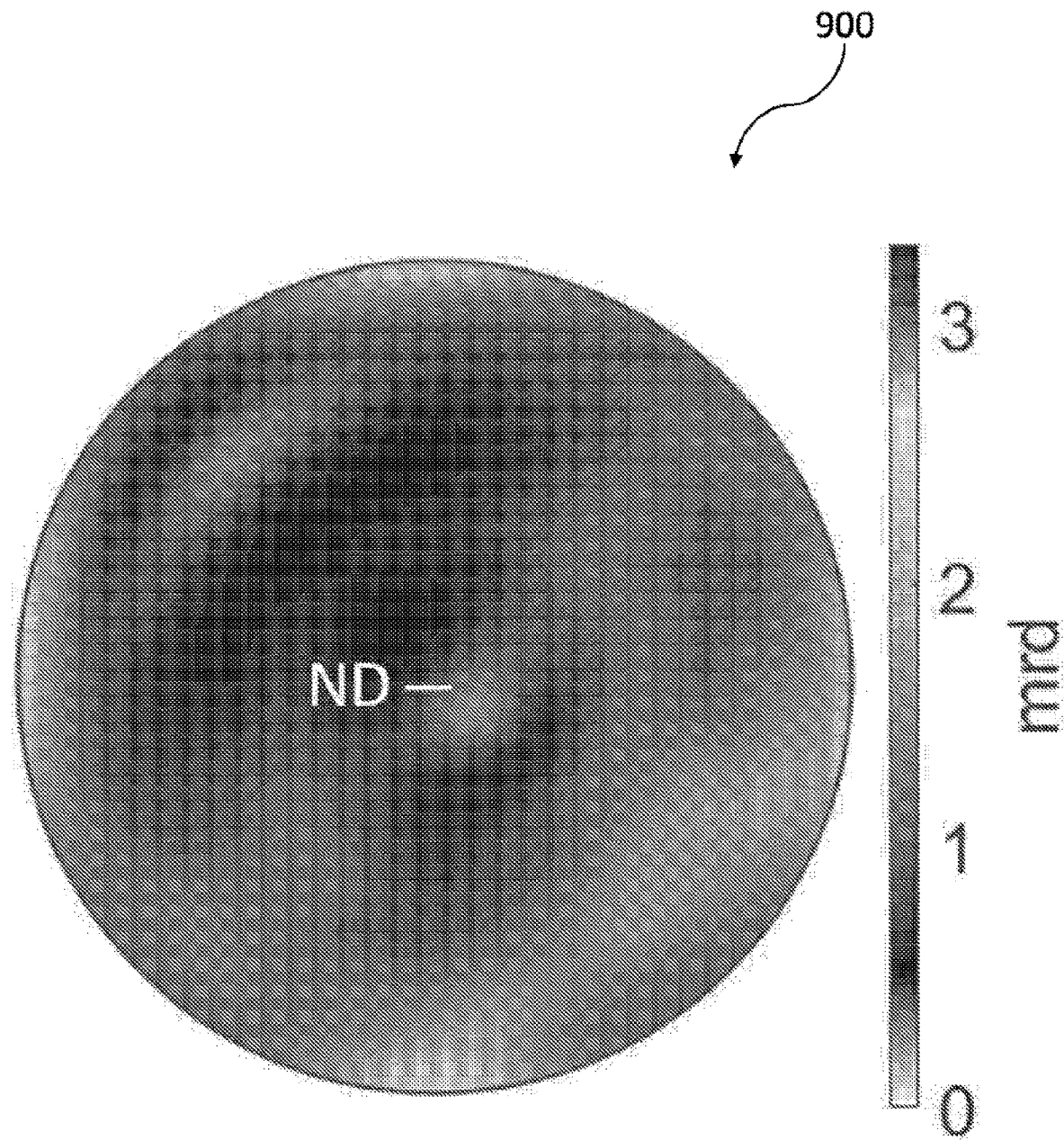

FIG. 1. Prior art—a sample with no surface abnormality.
FIG. 2. Prior art—a sample with a white layer present.
FIG. 3. Schematics of the process of the detection of surface abnormality.
FIG. 4. A diffractogram showing a diffraction pattern obtained as an output from a detector.
FIG. 5. Determination of white layer based on the peak intensity.
FIG. 6. Determination of white layer based on the peak broadening.
FIG. 7. An exemplary XRD pattern.
FIG. 8. An exemplary pole figure measurement for a sample with surface abnormality present.
FIG. 9. An exemplary pole figure measurement for a sample with no surface abnormality

DETAILED DESCRIPTION

FIG. 3 is a schematic representation of the process of detecting surface abnormalities in a sample. The arrangement consists of three basic elements: an emitter 301, a detector 302 and a processing unit (CPU) 303. In some embodiments, an emitter can be an X-ray source. It will be understood, that any X-ray source can be used without limitation to operate the method of the claimed invention, including but not limited to: copper, iron, molybdenum, chromium, manganese, silver or cobalt. Where the emitter is an X-ray emitter, the emitter is configured to generate X rays substantially in a range between substantially 10-60 kV. In an exemplary embodiment, the emitter 301 can generate X-rays in the range of substantially 30-50 kV, and optionally at substantially 40 kV.

Alternatively, the emitter 301 can be a laser source. Laser sources include high intensity lasers available in a variety of wavelengths, spanning from the ultraviolet to the near-infrared. By way of example, typical suitable laser wavelengths include: 244 nm, 257 nm, 325 nm, 364 nm, 457 nm, 473 nm, 488 nm, 514 nm, 532 nm, 633 nm, 660 nm, 785 nm, 830 nm, 980 nm, 1064 nm.

In yet another embodiment, the emitter 301 can be a neutron source capable of producing ionizing radiation in the form of hot, thermal or cold free neutrons that can be generated by any suitable process including: in a fission reactor (uranium nuclei break) or using a spallation source (proton bombardment of lead nuclei).

The detector 302 can be any suitable detector known in the art for detecting emission from a given emitter, such as a photon counting silicon strip detector. Optionally, the detector 102 can be one of a silicon based multichannel array detector of UV, visible and near-infra light, or a CCD (Charged Coupled Device). Alternatively, the detector 302 for neutron radiation can include gas-filled detectors, large area detectors or scintillators.

The processing unit 303 can be of any suitable type of computing device configured to run a software capable of processing a received output. Optionally, said software can also be configured to control and execute one or more stages of the process of detecting the surface abnormality without user input, i.e. automatically.

A machined sample 304 such as a machined alloy part is positioned in such a way that an incident beam 305 can reach the sample under an angle θ. The incident angle θ can be anywhere in the range between 0 and 90°. Said incident radiation is capable of interaction with the constituent matter of the sample 304 and after the interaction can be further scattered at a scattered angle θ'. Said scattered radiation 306 is then reflected into the detector 102 which produces an output in the form of a radiation pattern. This scattered radiation pattern is then further processed by the processing unit 303. The step of determining whether or not the surface abnormality is present 307 in the sample will be described in further detail below.

With the type of analysis process depicted on FIG. 3, a typical shape of the produced radiation pattern would be expected to be as shown in FIG. 4. FIG. 4 shows a graph 400 showing the output of the detector 303 depicted as an intensity of the scattered radiation on the scattered angle θ'. Peaks 401 and 402 are related to the measured structural property of the sample 204. Methods for detecting the abnormality from the graph 400 are described below.

One possible approach to estimate the presence of a surface abnormality in a sample is to use the width of the peak as a correlation to the internal structure of the sample 101. That is, the presence of the abnormality is dependent on the peak width. In the other words, the broader the peak, the higher the possibility of the defect in the internal structure. Preferably, full width at half maximum 403 (FWHM) can be used to assess peak broadening. It is however, understood that full width should not always be estimated at half maximum, and other fractional values can be used accordingly.

Another approach to estimate the presence of the surface abnormality is to use the ratio of peak intensities as a criterion of whether the surface abnormality is present. That is, if there are at least two obtained radiation peaks depicted as result of the irradiating the sample with the incident radiation beam, the ratio between the at least two peaks can be used as an indication of the presence of the abnormality. Referring to FIG. 4, a first peak 401 has a first intensity 404, and a second peak 402 has a second intensity 405, and the ratio can be derived as the intensity of the first peak divided by the intensity of the second peak. Depending on the material's formation mechanism and/or crystallographic structure, both approaches to estimating the presence of the surface abnormality (the peak width and intensity ratio approaches discussed above) can be used together or as a check (i.e. if one approach detects the presence of surface abnormality above a threshold limit then the second approach may be used as a check or verification).

In order to estimate the presence of the abnormality for either approach, a reference value from the sample with no abnormality is needed. That is, a threshold value above/below which no, or a tolerable level of, abnormality can be found, has to be set. This can be done by analysing the samples of a known structure, preferably but not necessarily pre-machined, where no surface abnormality is expected to be found. This allows a threshold value to be derived from the intensity and/or width of the one or more scattered radiation peaks and use this value as a term of comparison when assessing the presence of abnormalities in the samples with unknown structure.

It is understood that the tolerable level of surface abnormality (e.g. the maximum amount of white layer that is acceptable on the surface of a part without resulting in rejection of the part) may be set by the appropriate regulatory body or part manufacturer.

Once the threshold values from the reference samples are obtained, the following algorithm is employed to detect the surface abnormality.

The process of a typical procedure will now be described with reference to FIG. 5. In an illustrative example 501, the peak intensity ratio of a plurality of reference samples was used to determine a threshold value 502. A range of samples of unknown structure was then analysed, and the peak intensity values of the scattered radiation peaks were obtained from the detector output. If the peak intensity ratio of the sample exceeds the threshold value 502, the peak intensity ratio lies in a region 504 above the threshold 502, and therefore the surface abnormality is present. If, however, the peak intensity ratio is below the threshold value 502 and lies in the region 504 below the threshold 503, no, or a tolerable level of, surface abnormality can be detected.

With reference to FIG. 6, the peak widths of the plurality of reference samples were used 601 to determine a threshold value 602. A range of samples of the unknown structure are analysed, and the peak width values 604 of the scattered radiation peaks are obtained from the detector 302 output. If the peak width of the sample exceeds the threshold value 602, the peak width lies in a region above the threshold 602, and therefore an intolerable level of the surface abnormality is present. If, however, the peak width value 602 is below the threshold value 602 and lies in the region below the threshold 602, no, or a tolerable level of, surface abnormality can be detected.

In an exemplary embodiment, X-Ray diffraction (XRD) can be used to detect a surface abnormality. Being a bulk technique, with its penetration depth in the range of tens of microns, it is suitable for detecting surface abnormalities such as white layer of the thicknesses in the range of microns to the tens of microns. Generally, the method is suitable for detecting surface abnormalities to a depth in the range of the hundreds of microns.

An X-ray beam 305 generated by an emitter 301 such as cathode ray tube and filtered to produce monochromatic radiation hits the sample 304 placed in the path of the said incident beam 305. The source of monochromatic X-rays can be any one of copper, iron, molybdenum, chromium, manganese, silver or cobalt. Interaction of the X-rays with the sample produces a diffracted/scattered ray if the condition of Bragg's law (below) is met.

$$n\lambda = 2d \sin \theta$$

where n is an integer, $\lambda$ is a wavelength of the incident X-ray beam 305, d is a distance between atomic layers in the crystal lattice of the sample 304 and $\theta$ is an angle of incidence.

Specific crystallographic planes will diffract the X-ray beam 305 only at certain angles of incidence $\theta$. When systematically changing the angle of incidence (by scanning through a range of angles), the reflections from all the crystal planes can be detected by a detector 302. This output can be recorded as a diffraction pattern.

The diffraction pattern obtained from the surface of the material is known as a diffractogram that is plotted as a function of intensity v diffraction angles. The peaks 401, 402 on the diffractogram correspond to the crystal planes of the sample 304. Thus, by way of an example, for a nickel superalloy, a typical XRD pattern 700 is represented on FIG. 7. It can be seen that the intensity and the peak width of the reflections corresponding to crystal planes having notations (1 1 1) and (2 0 0) reflections for the processed (e.g. machined) samples 701 and 702 are different from that of the as received non-treated unprocessed sample 703 with no surface abnormality present. Thus, by collecting the data from the reference sample and/or samples 703 it is possible to obtain a threshold value of both the intensities 502 and the peak widths 602 of the sample with no, or tolerable level of, surface abnormality present. These threshold values can then be used for comparing with processed samples of the unknown structure.

If the intensity ratio of two peaks 504 corresponding to different crystal planes in the samples with unknown structure exceed the threshold 502 derived from the at least one of the plurality of reference samples with known structure, a surface abnormality such as white layer is considered to be present above tolerable level. If the ratio of the intensities of the two peaks is below the threshold value, no, or a tolerable level of, surface abnormality such as white layer can then be detected. A similar approach can be used for assessing the presence of white layer when peak widths 603, 604 is used as an assessment parameter against a threshold 602.

Alternatively, the detector can be arranged at a fixed angular position for a relevant crystal lattice plane (i.e. the detector in this instance is a fixed line detector). Using a fixed line detector, it is possible to measure over a limited range of angles and detect the peak intensity and width for a specific peak.

Alternatively, pole figure (PF) measurements can be carried out by rotating the sample within a Euler cradle whilst maintaining the same diffraction angle between the radiation transmitter and detector. By doing this, a full picture of the crystallographic texture (the orientations of all grains) can be built. FIGS. 8 and 9 are an exemplary embodiment of a typical PF measurement for a sample with basal texture wherein the basal plane is largely parallel to the machined surface (i.e. the basal pole pointed perpendicular to the machined surface). FIG. 8 shows results from a pole figure measurement 800 taken at the diffraction angle corresponding to the basal peak on a machined surface with a high measured multiples of random density (mrd) in the normal direction (ND) (in a sample with a surface abnormality present). With reference to FIG. 9, a sample without a surface abnormality (and therefore without basal orientation), has a smaller fraction of grains in that orientation in a pole figure measurement, so the measured mrd 900 is lower in the ND (see FIG. 9) relative to the sample with a surface abnormality present. Hence, pole figure measurements can provide equivalent information to previously described intensity measurements.

In another exemplary embodiment, a polychromatic beam 305 can be used in an energy dispersive mode as a source of photons. In this case, a scattering angle is fixed and the intensity is plotted as a function of energy. This allows determination of structural variations rapidly and with higher special resolution. In addition, as the scattering angle is fixed there is no need to use a goniometer to provide scans over different angles.

In yet another exemplary embodiment, a high intensity laser can be used as a source of radiation. This laser radiation is then focused onto the sample, interacts with the molecular vibrations and the scattered light is collected by means of lenses. A highly sensitive CCD detector 302 is then used to detect the scattered light, and the obtained output from the detector 302 is then processed by the processing unit 303. This scattered light is called Raman scattered light and it can provide information about the chemical and structural composition of the samples. The resulting pattern (Raman spectrum) is then plotted as an intensity of the scattered light vs frequency (or energy) of light. The peaks on the spectra can become narrower, broader or shift in frequency, these deviations from the expected position and shape are typically characteristic of the structural changes, i.e. stress, crystallinity or the amount of material present (in case of multi-component systems).

The invention claimed is:

1. A method of non-destructive detection of surface and near surface abnormalities in a metallic product, the method comprising:
   positioning a sample having a surface under a source of an incident radiation;
   irradiating the surface with the incident radiation from the source;
   detecting a scattered radiation;
   producing a radiation pattern from the detected scattered radiation;
   analysing the radiation pattern;
   producing an output indicative of the scattered radiation from the sample;
   comparing the output with a threshold value, the threshold value indicative of a maximum acceptable detected surface abnormality; and
   identifying the presence of a surface abnormality when the output exceeds the threshold value,
   wherein said surface abnormality is one or more of a white layer, white etching layer, amorphous layer, and thermo-mechanically deformed region; and
   wherein said incident radiation includes at least one of X-ray radiation and neutron radiation.

2. The method of claim 1, wherein the threshold value is derived from one or more reference samples with no surface abnormality present.

3. The method of claim 2, wherein the threshold value is derived from the intensity of one or more scattered radiation peaks of the one or more reference samples with no surface abnormality present.

4. The method of claim 3, wherein the threshold value is derived from the intensity ratio of one or more scattered radiation peaks.

5. The method of claim 1, wherein said surface abnormality is induced by machining, friction, shaping or forming.

6. The method of claim 1, wherein the output is an intensity value corresponding to an intensity of the detected scattered radiation.

7. The method of claim 1, wherein the output is derived from the intensity ratio of one or more scattered radiation peaks.

8. The method of claim 1, wherein the output is derived from a width of a scattered radiation peak corresponding to the scattered radiation.

9. The method of claim 1, wherein the threshold value is derived from one or more widths of the one or more scattered radiation peaks of the one or more reference samples with no surface abnormality present.

10. The method of claim 1, wherein the output is obtained by using filtered monochromatic X-rays.

11. The method of claim 10 wherein the output is obtained by scanning with a detector through a range of angles.

12. The method of claim 11 wherein the range of angles is $2\theta$, wherein $\theta$ is an angle of incidence.

13. The method of claim 10 wherein the output is obtained by arranging the detector at a fixed angle.

14. The method of claim 10, wherein the source of monochromatic X-ray is any one of copper, iron, molybdenum, chromium, manganese, silver or cobalt.

15. The method of claim 1, wherein the output is obtained using polychromatic X-rays.

16. The method of claim 1, wherein said sample comprises any alloy of the elements from the list: titanium, nickel, iron, aluminum.

* * * * *